United States Patent
Bachmann et al.

(10) Patent No.: US 9,757,415 B2
(45) Date of Patent: Sep. 12, 2017

(54) COMPOSITION COMPRISING SOLANUM GLAUCOPHYLLUM FOR PREVENTING AND/OR TREATING HYPOCALCAEMIA AND FOR STABILIZING BLOOD CALCIUM LEVELS

(71) Applicant: HERBONIS AG, Basel (CH)

(72) Inventors: Heinrich Bachmann, Wintersingen (CH); Walter Rambeck, Munich (DE)

(73) Assignee: HERBONIS AG, Basel (CH)

( * ) Notice: Subject to any disclaimer, the term of this patent is extended or adjusted under 35 U.S.C. 154(b) by 288 days.

(21) Appl. No.: 14/172,621

(22) Filed: Feb. 4, 2014

(65) Prior Publication Data

US 2014/0322322 A1 Oct. 30, 2014

Related U.S. Application Data

(62) Division of application No. 13/502,971, filed as application No. PCT/EP2010/065795 on Oct. 20, 2010, now abandoned.

(30) Foreign Application Priority Data

Oct. 20, 2009 (CH) ...................................... 1611/09

(51) Int. Cl.
| | | |
|---|---|---|
| *A61K 36/81* | (2006.01) | |
| *A61K 33/10* | (2006.01) | |
| *A61K 9/00* | (2006.01) | |
| *A61K 9/20* | (2006.01) | |

(52) U.S. Cl.
CPC ............ *A61K 33/10* (2013.01); *A61K 9/0068* (2013.01); *A61K 9/2009* (2013.01); *A61K 9/2027* (2013.01); *A61K 9/2054* (2013.01); *A61K 36/81* (2013.01)

(58) Field of Classification Search
None
See application file for complete search history.

(56) References Cited

U.S. PATENT DOCUMENTS

2009/0252805 A1* 10/2009 Piene ............................ 424/490

FOREIGN PATENT DOCUMENTS

| EP | 0689834 | * 3/1996 | ............... A61K 9/52 |
|---|---|---|---|
| WO | WO2009129818 | 10/2009 | |

OTHER PUBLICATIONS

Horst et al. (Role of Vitamin D in Calcium Homeostasis and its use in Prevention of Bovine Periparturient Paresis, Acta Vet. Scand. 2003, Suppl. vol. 97, pp. 35-50).*
Wehr et al. (Effect of Vitamin D-containing plant extract on osteoporosis, J. Steroid Biochem. & Mol. Bio., 2007, vol. 103, pp. 596-600).*
Goff in "Macromineral physiology and application to the feeding of the dairy cow for prevention of milk fever and other periparturient mineral disorders", Animal Feed Science and Technology, 2006, vol. 126, pp. 237-257.*
Worker et al. in "Enteque Seco", Calcification and Wasting in Grazing Animals in the Argentine, Nature, 1967, vol. 215, pp. 72-73.*
Roux, et al., "Solanum-glaucophyllum in Pregnant Cows Effected on Colostrum Mineral Composition and Plasma Calcium and Phosphorus Levels in Dams and New Born Calves", Annales de Biologie Animale Biochimie, vol. 19, No. 1A, Jan. 1, 1979, pp. 91-102.
Haussler et al., 1,25-Dihydroxyvitamin D3-Glycoside: Identification of a Calcinogenic Principle of Solanium Malocoxylon, Life Sciences, vol. 18, No. 10, May 15, 1978, 1049-1058.
Kunz et al., Solanum malacoxylon: Untersuchungen uber die Vertraglichkeit der zur Prophylaxe der Hypokalzamischen Gerbarlahmung empfohlenen Mengen [Solanum malacoxylon: studies of tolerance of doses recommended for the prophylaxis of parturient paresis], Beliner Und Muenchener Tieraerzliche Wochenschrift, vol. 94, No. 21, Nov. 1, 1981, pp. 421-424 XP008116775.

* cited by examiner

*Primary Examiner* — Bethany Barham
*Assistant Examiner* — Ping Cao
(74) *Attorney, Agent, or Firm* — K&L Gates LLP (57) ABSTRACT

The present invention provides a pharmaceutical and/or veterinary composition comprising a retard release formulation of a *Solarium glaucophyllum* preparation. The composition further preferably comprises a calcium source. The composition of the invention is suitable to prevent and/or treat hypocalcaemia. Furthermore, the composition is suitable to prevent milk fever in cows. Advantageously, the composition is administered only once before calving so as to prevent the occurrence of mil fever in cows.

19 Claims, 6 Drawing Sheets

COMPOSITION COMPRISING SOLANUM GLAUCOPHYLLUM FOR PREVENTING AND/OR TREATING HYPOCALCAEMIA AND FOR STABILIZING BLOOD CALCIUM LEVELS

PRIORITY CLAIM

This application is a divisional application of U.S. patent application Ser. No. 13/502,971, filed on Jun. 7, 2012, which is a National Stage of International Application No. PCT/EP2010/065795, filed Oct. 20, 2010, which claims priority to Swiss Patent Application No. 01611/09, filed Oct. 20, 2009, the entire contents of which are being incorporated herein by reference.

TECHNICAL FIELD

The present invention relates to a pharmaceutical and/or a veterinary composition comprising a *Solanum glaucophyllum* preparation, to methods for treating and/or preventing hypocalcaemia, milk fever, and/or parturient paresis, to methods for maintaining the level of calcium in blood and/or for normalizing blood calcium levels, and to compositions for use in such methods.

PRIOR ART AND THE PROBLEM UNDERLYING THE INVENTION

In a general aspect, the present invention addresses the problems of hypocalcaemia and suboptimal blood calcium levels in humans and animals, in particular in warm-blooded animals and in livestock. Calcium plays a fundamental role for bone formation, but also for the function of the musculature and the nervous system. Due to this important role, calcium concentration in blood is strictly regulated in humans and warm blooded (endotherm) animals. This regulation is known as homeostasis of calcium. Increased blood calcium levels (hypercalcemia) may cause convulsions, while too low calcium levels may cause paralysis of limbs and later of the heart muscle. When untreated, this may cause death.

For example in female cattle, blood calcium values generally drop strongly around calving because of the suddenly start of the milk production, which removes calcium from the maternal blood circulation. This calcium cannot always be replaced quickly enough from food and from the bones. As a consequence, especially older and high-producing milk cows may suffer from milk fever. Milk fever, peri-parturient hypocalcaemia or parturient paresis is a disease of milk producing cattle, such as cows, sheep and goats, in particular dairy cows, and is most common in the first days of lactation. If calcium concentration in blood falls below 1.6 mmol/l, the cow may downer. Affected individuals generally suffer from general weakness (paresis), loss of appetite, paralysis and in the worst case, death, generally due to heart failure. Clinically manifest milk fever may only be treated by injection of a calcium solution. However, also sub-clinical hypocalcaemia is associated with follow-up or secondary diseases, such as mastisis, ketosis, dislocatio abomasi, traumatic birth, and retention secundinarum. As becomes clear from the above, the occurrence of hypocalcaemia in milk producing animals, in particular livestock is associated with additional costs and has thus an important economic impact.

Several treatments and prophylaxis have been proposed to address hypocalcaemia, in particular post-parturient hypocalcaemia, such as milk fever in cow.

One possibility is the administration of 1,25-dihydroxyvitamin $D_3$ (1,25-$(OH)_2$ vitamin $D_3$) obtained by synthetic production, for example. This hormonally active form of vitamin $D_3$, also known as calcitriol, is part of the regulation mechanism of blood calcium levels and is produced in the kidneys. The physiologic regulation and production of this hormone is relatively slow and may not be sufficient under certain conditions, in particular during the start of milk production in the mammals. 1,25-$(OH)_2$ vitamin $D_3$ induces an increase of blood calcium levels by increasing calcium uptake from the gut, decreasing the transfer of calcium from blood to the urine by the kidney and increasing the release of calcium from bone into blood. However, the administration of 1,25-$(OH)_2$ vitamin $D_3$ is not without problems. One problem is that it can be counter-productive due to its homeostatic regulative function in the body, when administered too early.

In a publication of Horst et al. (Recurring hypocalcemia of bovine parturient paresis is associated with failure to produce 1,25-dihydroxyvitamin D. Goff J P, Reinhardt T A, Horst R L. Endocrinology. 1989 July; 125(1):49-53) the authors noticed a very narrow time window for the administration of 1,25-$(OH)_2$ vitamin $D_3$ for obtaining a beneficial result. However, since the exact day or time of birth cannot be predicted with certainty, there is the risk that the narrow time frame is missed when administrating 1,25-$(OH)_2$ vitamin $D_3$ and the abovementioned counterproductive effect is obtained. Therefore, it would be advantageous to have a larger time frame for administrating 1,25-$(OH)_2$ vitamin $D_3$ to a cow before birth, so as to increase the possibility of successful prevention and/or treatment of milk fever and/or to maintain blood calcium levels before and after birth. Furthermore, it would of course be advantageous to administrate a medicament only once and not several times before and/or after birth.

An important problem of 1,25$(OH)_2$ vitamin $D_3$ administration is the known narrow ratio between the desired effect and unwanted side effects. This problem is described in more detail in WO2009/129818.

Another possibility for preventing hypocalcaemia, in particular post-parturient hypocalcaemia is the administration of calcium directly. For example, Bovikalk® is a commercially available calcium preparation in the form of a bolus for preventing and treating milk fever in cows. This product comprises calcium in the form of calcium chloride and calcium sulphate and is dissolved within 30 minutes following administration. One disadvantage of this product is the need for repeated administration. The Bovikalk® bolus needs to be orally administrated before and also several times after calving to be effective. Since the administration of a bolus to a cow requires time and efforts, it would be advantageous to have a product that needs only to be administered once. Another disadvantage of this product is linked to the presence of the acidic form of calcium. Although the bolus has a wax-based coating, there are reports that the bolus becomes stuck in the oesophagus or is disadvantageously positioned in the first stomach. Depending on the position of the bolus within the gastro-intestinal tract of the animal, damages to the wall of the oesophagus or the first stomach and even perforation may occur in some cases.

A further disadvantage of direct calcium administration is again that the time period for the necessary administration before birth is relatively short. Too early administration of calcium is counterproductive, due to the adjustment of the body regulation to excess of calcium.

Other methods of treatment and prevention of hypocalcaemia in cows include the DCAC-method, which is a particular diet reducing blood pH and that is poor in calcium and which is given to the cow in the last weeks before calving. While this preventive measure is considered effective, it requires a particular feeding system during several weeks. Similarly, the addition of calcium binders such as zeolite or similar ion exchangers to food requires treatment periods of several weeks before birth.

Also the administration of certain plants containing vitamin $D_3$ has been proposed, such as *Solanum glaucophyllum*, *Cestrum diurnum* and/or *Trisetum flavescens*. However, again several applications are necessary in order to hit the ideal moment of administration before birth. Furthermore, by application of uncontrolled materials (concentrations, presence of other plant components), undesired side effects may occur.

In summary, the present invention addresses the problem of hypocalcaemia in all vitamin D dependent animals and in humans and in particular of milk fever in milk producing livestock, in particular cows, sheep and goats. One objective of the present invention is to provide an effective pharmaceutical and/or veterinary composition that needs only be administrated once and which is suitable to prevent and/or treat hypocalcaemia and in particular milk fever. Furthermore, it is an objective to provide a composition that can be administered within a larger time frame before giving birth without increasing the occurrence of counterproductive effects. Furthermore, it is an objective to avoid undesired side effects of presently commercialised products, for example products containing synthetic $1,25\text{-(OH)}_2$ vitamin $D_3$ or calcium chloride, for example.

The present invention addresses the problems depicted above.

SUMMARY

The inventors surprisingly found that a composition comprising a *Solanum glaucophyllum* (*S. glaucophyllum*) preparation is suitable to address the problems underlying the invention depicted above. In particular, the *S. glaucophyllum* preparation comprises glycosides of $1,25\text{-(OH)}_2$ vitamin $D_3$. This glycosidic form of $1,25\text{-(OH)}_2$ vitamin $D_3$ does to a remarkably lesser degree produce the side effects reported for synthetic $1,25\text{-(OH)}_2$ vitamin $D_3$.

Accordingly, in an aspect, the present invention provides a composition comprising at least a formulation of a *S. glaucophyllum* preparation. The composition is preferably a pharmaceutical and/or veterinary composition.

In another aspect, the present invention provides a pharmaceutical and/or veterinary composition comprising at least a retard release formulation of a *S. glaucophyllum* preparation.

In an aspect, the present invention provides a pharmaceutical or veterinary composition comprising a retard release formulation comprising a *S. glaucophyllum* preparation, wherein said retard release formulation completely releases $1,25\text{-(OH)}_2$ vitamin $D_3$-glycosides contained in said preparation within a time period lasting at least 4 hours or longer. Preferably, said composition further comprises a calcium source.

In an aspect, the present invention provides a pharmaceutical or veterinary composition comprising a first formulation comprising a *S. glaucophyllum* preparation and a second formulation comprising a *S. glaucophyllum* preparation, wherein said first formulation is characterised in that it releases at least one active principle present in said preparation more slowly upon administration than said second formulation. Preferably, the composition comprises a calcium source.

In another aspect, the invention relates to the composition of the invention for use as a medicament.

In an aspect, the invention relates to the composition of the invention for treating and/or preventing hypocalcaemia.

In an aspect, the present invention relates to the composition of the invention for increasing the level of calcium in blood.

In an aspect, the invention relates to the composition of the invention for normalizing blood calcium levels.

In an aspect, the present invention relates to the composition of the invention for maintaining normal and/or healthy calcium levels in blood.

In an aspect, the present invention relates to the composition of the invention for avoiding and/or preventing deficiencies of calcium in blood.

In an aspect, the present invention relates to the composition of the invention for treating and/or preventing parturient paresis.

In an aspect, the present invention relates to the composition of the invention for treating and/or preventing and/or milk fever, in particular in cattle.

In an aspect, the present invention provides methods of treatment and/or for the prevention of any one condition and/or disease disclosed in this specification.

In an aspect, the present invention provides a method for treating and/or preventing hypocalcaemia, the method comprising the step of administering to a subject the composition of the invention.

In an aspect, the present invention provides a method for treating and/or preventing parturient paresis and/or milk fever, for example prenatal parturient paresis, the method comprising the step of administering to a subject the composition of the invention.

In an aspect, the present invention provides one or more methods selected from the group of: a method for (1) maintaining normal and/or healthy blood calcium levels; (2) normalizing blood calcium levels; (3) increasing blood calcium levels; (4) avoiding calcium deficiencies in blood; (5) avoiding insufficient calcium levels in blood.

Further aspects and preferred embodiments of the invention are defined herein below and in the appended claims. Further features and advantages of the invention will become apparent to the skilled person from the description of the preferred embodiments given below.

DETAILED DESCRIPTION

The present invention relates to a composition comprising a *S. glaucophyllum* preparation.

A "*S. glaucophyllum* preparation", for the purpose of the present invention, may be any preparation obtained from the plant *Solanum glaucophyllum* containing glycosides of 1,25 (OH)$_2$ vitamin D$_3$. Preferably, the preparation is obtained from the leaves of *S. glaucophyllum*. The 1,25-(OH)$_2$ vitamin D$_3$-glycosides are the active principle present in *S. glaucophyllum*. The glycosidic form of 1,25-(OH)$_2$ vitamin D$_3$ is supposed to require break-up of the glycosidic bond in the gastro-intestinal tract, for example in the rumen of ruminants, before it can be absorbed. The *S. glaucophyllum* preparation may be referred to herein as the plant preparation.

1,25-dihydroxyvitamin D$_3$, also known as calcitriol and 1,25-dihydroxycholecalciferol, is the hormonally active form of vitamin D. Herein below, any one of these designations and also the designation 1,25-(OH)$_2$ vitamin D$_3$ are used.

According to an embodiment, the *S. glaucophyllum* preparation is prepared from dried leaves. For example, dried leaves may be ground, comminuted or in any other way transformed into a powder. The powder may be then directly used for the preparation of the composition of the invention.

According to an embodiment, said *S. glaucophyllum* preparation is in particular selected from the group of comminute and/or powdered dry leaves of *S. glaucophyllum*, an extract prepared from *S. glaucophyllum* leaves and from a combination of both of the aforementioned.

In accordance with the above, the *S. glaucophyllum* preparation may be an extract prepared from *S. glaucophyllum*, preferably from plant material, such as the whole plant, the aerial plant parts, and/or the leaves. The plant material is preferably dried. An extract may be prepared as is disclosed, for example, in WO 2009/129818. In particular, an extract may be obtained, for example, by maceration or by percolation, for example, using a suitable solvent. As a solvent, a mixture of water and a lower alcohol (preferably ethanol) or acetone at the ratio (v:v) in the range of 80:20 to 25:75 (water: alcohol/acetone) may be used, for example.

In a typical extraction process, the leaves and the solvent solution are mixed at a weight ratio of 1:5 to 1:15 (leaves: solvent), for example, and the active principle is thus extracted by stirring the mixture for about 6 to 24 hours at 25 to 55° C., for example. The process may be repeated following removal of the solvent, for example by filtration and adding new solvent.

According to an embodiment, percolation is used for extracting the active principles. In this case, any suitable commercially available equipment may be used. For example, the plant material may be percolated in a percolator comprising 1 to 10, preferably 4 to 8 cyclically connected tanks, at 35-55° C. for 4 to 8 hours.

One or more antioxidants may be added at 0.05 to 1 wt. %, preferably 0.05 to 0.2 wt. % of dry matter to the plant extract, for example to the liquid phase following percolation. Examples are ascorbinic acid, gallates, BHA and BHT. This may reduce the undesired browning of the liquid phase and of the extract. Browning may also be reduced, alternatively or in addition, by adjusting the pH of the liquid phase to a value of 5.5 to 6.5 using, preferably, a food grade acid, such as citric acid, acetic acid, formic acid, sulfuric acid, hydrochloric acid, phosphoric acid, for example.

The solvent of the liquid phase or phases is preferably reduced and/or at least partially removed, by drying, evaporating and/or under vacuum, for example using a thin-layer evaporator to a concentration of approximately 10-50%, more preferably 30-40%, most preferably about 35% dry matter, to obtain a concentrated liquid extract.

This concentrated liquid extract may be analyzed with respect to the presence of any undesired alkaloids. For example, it may be checked if any one or more of solanine, chaconine and/or solasodine can be detected in the extract. Solanine, such as a-solanine, is a glycoalkaloid poison that may be present in species of the nightshade family (Solanaceae). Alpha-chaconine is a steroidal glycoalcaloid, which has insecticidal and fungicidal properties. Solasodine is also a poisonous glycoalcaloid.

If any one of the aforementioned alkaloids is detected, it may be removed by guiding the concentrated liquid extract over a suitable column, for example. For example, the liquid extract may be chromatographed using a column comprising a strongly or weakly acidic ion exchange resin, which is preferably equilibrated in the $H^+$ form. This may be a continuous or a batch-wise process.

According to an embodiment, said preparation of S. glaucophyllum is characterised in that glycosides of 1,25-$(OH)_2$ vitamin $D_3$ are the only active form of vitamin $D_3$ present in said preparation and/or in that alkaloids occurring sometimes in Solanum species are substantially absent, said absent alkaloids being preferably one, two or all three selected from solanine, chaconine and solasodine. "Substantially absent", in this regard, means that said alkaloids may be present below the detection level of commercially available detection methods. Preferably, said alkaloids are totally absent in said preparation.

Also the concentration or content of the active principles, 1,25-$(OH)_2$ vitamin $D_3$-glycosides, in the extract may be determined at this stage. These concentrations may vary between plants and depending on climatic conditions and/or cultivation site and need therefore to be determined so as to control the dose.

The concentrated liquid extract, or, if guided over a column, the eluate of the concentrated liquid extract is then preferably heat-treated, for example by UHT treatment, so as to remove germs.

Before the final drying step, additives, fillers, in particular carbohydrates and derivatives thereof, such as, for example, maltodextrin and the like may be added in suitable amounts. In this way, the concentration of the active principle (1,25-$(OH)_2$ vitamin $D_3$-glycosides) may be adjusted to a desired value. Additives may be added for improving or adjusting stability, processability and/or plasticity, for example.

Thereafter, the concentrated liquid extract may be dried to a final water content of below 10%, preferably below 7%, even more preferably below 6%, most preferably below 5%. This may be achieved by spray- or vacuum belt drying, for example.

The dried extract above may be directly used in the composition of the invention or may be further processed, for example to obtain one or more formulations exhibiting controlled release characteristics. For example, the extract can be used directly as an instant release formulation. According to another example, the dried extract (or also the liquid concentrated) may be used to prepare specific instant and/or retard release formulations.

As mentioned above, the concentrations of 1,25-$(OH)_2$ vitamin $D_3$-glycosides in S. glaucophyllum may vary due to different factors, which as such may not all be controlled always. Therefore, it is advantageous to use a S. glaucophyllum sort or variety having generally a high content of 1,25-$(OH)_2$ vitamin $D_3$-glycosides, in particular in the leaves. According to a preferred embodiment, said S. glaucophyllum is selected from a wild type or cultivated form of S. glaucophyllum, preferably from the plant sort 'HERVIT' (according to the Community Plant Variety Certificate EU25473 of Jun. 22, 2009). Of course, other sorts and/or varieties, such as those that are derived from said 'HERVIT' sort, may have an ever higher content of 1,25-$(OH)_2$ vitamin $D_3$-glycosides and may thus be also or preferably used.

According to an embodiment, the composition of the present invention is intended for oral administration.

According to an embodiment, the composition comprises at least one, for example a first formulation, that comprises said S. glaucophyllum preparation, wherein said formulation release the active principle present in the preparation in a retarded or slow release manner.

Retard or slow release preferably means that said formulation has completely released said active principle not before but possibly after a period lasting at least 4 hours, at least 6 hours, preferably at least 8 hours, more preferably at least 10 or at least 12, 14, 16 hours, preferably at least 18 hours, more preferably at least 20 hours, and most preferably not before the expiry of 22, preferably 24 hours following administration of the composition. In accordance with the invention, the active principle may be released constantly but in a retarded manner over time and said release is completed, with respect to the retard release formulation, not before the indicated time.

In other words, the retard release formulation retains and thus prevents release of at least some of the active principle for a period of 4, 6, 8, 10, 12, 18, 20, 22, 24 hours.

For the purpose of the present specification, the expressions "slow release", "retard release", "retarded release", "sustained release" and the like have the same meaning. Generally, the expression "retard release" is used to refer to all of them.

The release duration or the duration of release retention refers in principle to release in the gastrointestinal tract following administration. For determining the release in a controlled experimental setting, an in vitro release text using a dissolution medium may be employed as an approximation. Release of 1,25-$(OH)_2$ vitamin $D_3$-glycosides may be determined by measuring absorbance in the test recipient at 300 nm, online, for example, or by determining the concentration of the active principle present in the experimental solution in repeated measurements over time (both experiments are conducted in the examples). More specifically, the release time is determined using the current US Pharmacopeia (USP) dissolution test, disclosed in the USP, in particular Chapter Dissolution <711>. The dissolution medium is filtered (0.45 μm porosity filter) and deaerated water (USP deaeration procedure) and has a temperature of 37° C. at the beginning of the test (see: Dissolution Toolkit Procedures for Mechanical Calibration and Performance Verification Test Apparatus 1 and Apparatus 2 Version 2.0, Mar. 22, 2010).

According to an embodiment, said retard release or said first formulation comprises said S. glaucophyllum preparation with at least one excipient, which exhibits retard release characteristics.

According to an embodiment, said retard release characteristics are obtained by including said S. glaucophyllum preparation, for example said extract, in a matrix or by coating said preparation containing said extract with an excipient that releases said active principle in a retarded manner. According to an embodiment, said matrix comprises components that are not or hardly soluble in water and/or wherein said excipient of said coating releases said active principle by diffusion through said coating and/or by way of enzymatic decomposition in specific compartments of the digestive tract. According to an embodiment, release may occur due to erosion in presence of water and/or digestive liquids.

There are many different ways in which the release of the active principle may be retarded in accordance with the invention and the invention is not intended to be limited to a particular retard release formulation. As mentioned, the plant preparation may be embedded in a matrix containing components and/or excipient that prevent, hinder or slow down the dissolution and/or erosion of the formulation once administered. Components that are only partially or not soluble in water may be added in the formulation. An example of an excipient that may be used for preparing the retard release formulation is Eudragit® RS or RL (copolymers of acrylic and methacrylic acid esters with a low content in quaternary ammonium groups). This copolymer may be used as a matrix component, for example in tablets, or used as a coating. Further below, examples of retard release formulations are provided.

According to an embodiment, the coating of said plant preparation and/or of said retard release formulation comprises an excipient, which is resistant to the digestive liquid of the stomach, but which is decomposed when in contact with bile and/or with pancreatic juice. For example, fats and other fatty acid esters may be used in the coating to this end.

According to an embodiment, the composition comprises at least one S. glaucophyllum preparation in the form of an instant release formulation. The expression "instant release formulation" refers to any formulation which does not specifically retard release and to formulations which contain ingredients that speed up release of the active principle contained in the formulation. For the purpose of the present invention, an instant release formulation encompasses normal- and fast release formulations. In an instant release formulation in accordance with the present invention, the active principle is released from the formulation within a time period of 8 hours, preferably within 6 hours, more preferably within 5, 4, 3, 2 hours or even within 1 hour, for example following administration. Also in case of the instant release formulation, the measurement of the complete release duration may be determined by an in vitro experiment as disclosed elsewhere in this specification.

The soluble, dry extract described above is soluble readily in water and may thus be directly used as an instant release formulation for the purpose of the present invention. The instant release may also comprise excipients that increase or accelerate release, such as disintegrants, which may cause rapid swelling and disintegration of the formulation, for example a tablet or a pill, comprising it. Examples of such disintegrants are sodium salts of carboxymethylcellulose and carboxymethylated starch, crosslinked polyvinylpyrrolidone (PVP), or simply starch.

The instant release formulation, and/or the retard release formulation may, independently, further comprise binding materials and fillers as is usual in the art.

Of course, further additives may be added in order to facilitate the production of the particular retard and/or instant release formulation such as the tablet and/or the coating, such as diluents, emollients, plasticizers, detackifiers, anticaking agents, wetting agents and the like.

According to a preferred embodiment, the composition of the invention comprises a first formulation comprising a *S. glaucophyllum* preparation and a second formulation comprising a *S. glaucophyllum* preparation, wherein said first formulation is characterized in that it releases at least one active principle present in said preparation more slowly upon administration than said second formulation. Accordingly, said first formulation may be a retard release formulation and said second formulation may be an instant release formulation as discussed elsewhere in this specification.

According to an embodiment, said second formulation comprises said *S. glaucophyllum* preparation and one or more excipient, which rapidly releases said active principle. For example, rapid release may occur following contact with water and/or digestive liquids, for example in the first stomach or rumen of ruminants or in the stomach of monogastric animals.

According to a preferred embodiment, the composition of the invention comprises a calcium source. Any suitable calcium source comprising preferably a salt of calcium may be used. Calcium sources that have a high bioavailability are preferred. According to a preferred embodiment, the calcium source is dolomite. More preferably, the calcium source is heat-activated dolomite. This form of calcium has a surprisingly high bioavailability with a high or even major part of the ingested calcium being absorbed in the gastrointestinal tract. Dolomite and heat-activated dolomite are commercially available.

Dolomite is particularly advantageous because it provides readily absorbable calcium, and, in addition, magnesium, which is beneficial for the process of muscle contraction during labour at calving.

Furthermore, dolomite is suitable to increase the density of the composition of the invention. According to an embodiment, the composition of the invention, and/or the first formulation and/or the retard release formulation has a density of $\geq 1.1$, preferably $\geq 1.15$ or $\geq 1.2$, or more preferably $\geq 1.25$, even more preferably $\geq 1.3$. The high density is particularly relevant for the retard release formulation, as detailed below.

Accordingly, dolomite may be added to or part of the first formulation, to the second formulation or to both. Alternatively, dolomite may be added to the composition separately.

The advantage of having a density $\geq 1$ applies in particular to ruminants, which may otherwise rehash and ruminate and thereby also physically destroy the retard release formulation by chewing, so that the retard release characteristics are lost. However, if the density is adjusted, at least of the retard release formulation, to the indicated values, the respective formulation will not be rehashed but remains in the rumen or gastrointestinal tract and the active principle is released in a retarded manner as desired.

Dolomite is thus a particularly advantageous additive in that it adds bioavailable calcium, it assist birth labor and increases the density of the formulation containing it.

The composition may be provided in any suitable ingestible form. According to an embodiment, the composition of the invention is provided in the form of any one or more of the group selected from: a bolus, a capsule, a granular composition, a pellet, a tablet, a gel and a powder, for example a compacted powder.

For example, the composition of the invention may be added in the form of a powder to the normal food and taken up with this food.

According to an embodiment, the *S. glaucophyllum* preparation and/or the instant and/or retard release formulations are provided in the form of a gel.

According to an embodiment, the formulations and/or preparations are homogenously pressed or are compartmented in different layers or are cylindrically arranged. In this latter case, the retard release formulation is preferably provided in the centre of the cylinder, for example in the form of an inner cylinder, the instant release formulation being provided as an outer cylinder encasing the retard release formulation, for example.

If the composition is to be applied to an animal, for example a cow, it may be provided in the form of a bolus. A bolus may be administered using a commercially available bolus applicator. Boluses are routinely used for administrating nutrient supplements and medicaments to cattle.

According to an embodiment, the composition is provided in the form of a layered bolus, pellet or tablet comprising at least two layers, one layer being or comprising the instant release formulation and the other layer being or comprising the retard release formulation.

According to another embodiment, the formulations are provided in the form of tablets. For example, the instant release formulation may be provided in the form of tablets or capsules that are different from the tablets of the retard release formulation. Any one of the two formulations may comprise the calcium source, in particular dolomite, or the calcium source may be provided also in the form of separate tablets. All tablets may, for example, be filled in a bolus capsule, optionally filled with a suitable filler or binder, and administered in this form to the animal.

Tables 1-3 below show exemplary instant release formulations (Table 1) and sustained release formulations (Tables 2 and 3), which are provided in the form of separate tablets containing a dried *S. glaucophyllum* extract as disclosed in the examples and elsewhere in this specification. Exemplary product names of ingredients that may be used for producing the tablets are also indicated. In some lines of the tables, for example with respect to the disintegrants, different products that may be used in the alternative or in combination are disclosed.

TABLE 1

Exemplary formulations of instant-release tablets (IR-tablets)
Density: 1.2-2 g/ml; diameter: for example about 8 mm

| Ingredients | weight per Tablet | function |
|---|---|---|
| 1. dry extract of *S. glaucophyllum* | 50 mg | |
| 2. dolomite CaMg[CO$_3$]$_2$ | q.s. ca. 0-350 mg | density regulation Mg and Ca source |
| 3. sodium salt of carboxymethylated starch (Explotab ®, Vivastar ®, Primojel ®); 2-8% | 8-32 mg | disintegrants |
| crosslinked polyvinylpyrrolidone (Kollidon CO); 0.5-5% | 2-20 mg | |
| sodium salt of earboxymethylcellulose (Ac-Di-Sol ®, Vivasol ®); 1-5% | 4-20 mg | |
| starch (Starch 1500); 2-10% | 8-40 mg | |
| 4. PVP; HPMC (hydroxypropylmethyl-cellulose) 0-10% | 0-40 mg | binders |
| 5. lactose/ microcrystalline cellulose | 0-170 mg (q.s.) | fillers |
| Total | ca. 400 mg | | q.s.: as deemed useful

TABLE 2

Exemplary formulations of retard release tablets (SR-tablets), the matrix only (coating described further below). Exemplary concepts 1 and 3: tablets may have, for example 8 mm diameter and a density of >2 g/ml

| Ingredients | weight per Tablet | function |
|---|---|---|
| 1. dry extract of *S. glaucophyllum* | 40-80 mg | |
| 2. dolomite CaMg[CO$_3$]$_2$ | q.s. ca. 280-340 mg | density regulation Mg and Ca source |
| 3. PVP; HPMC (hydroxypropylmenthyl-cellulose) | 0-20 mg | binder |
| 4. lactose/ microcrystalline cellulose | 0-60 mg (q.s.) | filler |
| Total | ca. 400 mg | |

TABLE 3

Exemplary formulations of retard release tablets (SR-tablets), the matrix only (coating described further below). Exemplary concept 2: tablets may have, for example 3 mm diameter and a density of about ≥1.2//ml

| Ingredients | Masse pro Tablette | Funktion |
|---|---|---|
| 1. dry extract of *S. glaucophyllum* | 2 mg | |
| 2. dolomite CaMg[CO$_3$]$_2$ | q.s. ca. 1-3 mg | density regulation, Mg and Ca source |
| 3. PVP; HPMC (hydroxypropylmethyl-cellulose) | 0-1 mg | binder |
| 4. lactose/ microcrystalline cellulose | 6-9 mg (q.s.) | filler |
| Total | ca. 12 mg | |

The tablets described in Tables 2 and 3 are preferably coated so as to retard the release of the 1,25-(OH)$_2$ vitamin D$_3$-glycosides.

In accordance with concepts 1 and 3 (Table 2), the coating may comprise or be composed of, for example poly(meth)acrylate-methyl/ethyl/2-timethyl amino ethyl ester-copolymerisate (Eudragit® RL, Eudragit® RS) with HPMC (hydroxypropylmethylcellulose), lactose or polyvinyl lacetate for providing pores for the adjustment of the release speed in concepts 1 and 2; as well as detackifiers (for example talc), wetting agent (for example Tween® 80) and plasticizers (examples: diethyl phthalate, triethyl citrate).

In accordance with the concept 2 above (Table 3), the formulation may be processed to tablets or capsules. f processed to tablets, they may be coated, for example, with polymethacrylate-methyl/butyl12-dimethyl aminoethyl ester-copolymerisate (Eudragit® E) with suitable wetting agents (for example sodium lauryl sulfate), pasticizers (stearic acid) and anti-caking agents (for example talc).

If processed to capsules, the coating may comprise and/or be composed of ethyl cellulose (Aquacoat®, Surelease®) with plasticizer (examples: diethyl phthalate, triethyl citrate), wetting agents (for example Tween® 80) and anti-caking agents (for example talc), if necessary.

As mentioned below, the composition of the invention may comprise a retard release formulation and an instant release formulation. referably, the two formulations are contained in the composition at a weight ratio of 1:9 to 9:1, 2:8 to 8:2, 3:7 to 7:3, 4:6 to 6:4 and preferably about 1:1, expressed as weight ratio of 1,25-(OH)$_2$ vitamin D$_3$-glycosides present in the instant-release formulation with respect to the retard release formulation.

With the goal of keeping the administered dose of 1,25-(OH)$_2$ vitamin D$_3$-glycosides constant, the following examples using the tablets/capsules of concepts 1 to 3 above are given, in which the total dose is held at 10 g per dried plant extract.

Concept 1: IR: 4 g; SR: 6 g; =>80 IR-tablets and 100 SR-tablets.

Concept 3: IR: 4 g; SR: 6 g; _>80 IR-tablets and 100 SR-tablets.

Concept 2: IR: 6 g; SR: 4 g; =>120 IR-tablets and 2000 SR-tablets.

The above examples illustrate how the skilled person can control the amount of 1,25-(OH)$_2$ vitamin D$_3$-glycosides that is administered in a retard release and/or in an instant release formulation. It is noted, that the concentration of 1,25-(OH)$_2$ vitamin D$_3$-glycosides in the dried plant extract is controlled and/or adjusted before the final drying step as disclosed elsewhere in this specification.

The composition and/or formulations disclosed in this specification may be used as medicaments and in methods of prevention and/or treatment of conditions, such as diseases.

The compositions may in particular be used for preventing suboptimal blood calcium levels, for increasing blood calcium levels, for avoiding and/or preventing calcium deficiency, for maintaining healthy, average and/or normal blood calcium levels, in particular in cattle (in particular in cows, goat, and sheep) and also in humans.

The expression "serum calcium levels" and the like preferably refers to total calcium content in blood, including free dissolved as well as protein bound calcium, as may be determined, for example, following collection of total calcium from a blood sample, by flame photometry.

Accordingly, the composition of the present invention may be used to treat and/or prevent hypocalcaemia, in particular in cattle, in particular cows, goat, and sheep. The composition may also be used to treat and/or prevent hypocalcaemia in humans. Hypocalcaemia may have many causes and origins, including, for example, eating disorders, hereditary diseases, vitamin D deficiency, decreased sun exposure, just to mention a few arbitrarily selected causes.

In cattle, hypocalcaemia may concur with calving or may occur shortly before and/or after birth, due to the onset of the mammary milk production. In cows, milk fever may occur, which in severe cases, may lead to death of the cow. Milk fever causes important damages.

Accordingly, the composition and formulations disclosed in this specification may be used to treat and/or prevent milk fever, in particular in milk producing and/or older cows, preferably in the period around and/or after calving.

The presence of a retard release formulation and/or a combination of a retard release and an instant release formulation in the composition is particularly advantageous for the prevention and/or treatment of milk fever. Thanks to the composition of the invention, the composition may be administered only once, in one single treatment, preferably shortly before giving birth. As discussed above, a single administration of calcium or synthetic 1,25-(OH)$_2$ vitamin D$_3$ could be counterproductive if the moment of administration is not optimal, for example too long time before calving. Thanks to the composition of the invention, the time window within which the composition can be administered becomes larger, making a successful treatment more likely. This applies also and in particular if the composition is only administered once. The longer time window before birth is important, because the exact time of calving can, of course, not always be accurately predicted. The exact length of the gestation period is, of course, subject to a certain variation.

It has been observed that the composition of the invention can be effective if administered for up to 3 days ante partum, preferably up to 4, 5, 6, 7, 8, 9, 10 days ante partum (before birth) or at the first signs of imminent calving. If administered in suitable amounts, a single administration of the composition of the invention may increase blood calcium levels for up to 3-10 days.

According to an embodiment of the method and/or of the composition of the invention, the composition is administered as a single administration dose to a gestating mammal before giving birth, preferably in the period of up to 9 days before birth, 8 days to 0.5 hours, 7 days to 1 hour before giving birth, preferably 96 to 12 hours before birth, most preferably 72 to 24 hours birth or at the first signs of imminent birth. "Before birth" or "before calving" for the purpose of the present specification, refers to the period ending with the onset of the birth process, preferably to the period lasting up to the first contraction/labor pains.

In a gestating cow, the composition is preferably administered as a single dose 2 to 4 days before calving. The indicated time intervals are preferably determined on the basis of an estimation of the average gestation period. If, following administration of the composition 5 or more days lapse without calving taking place, a further application dose (typically a bolus) is preferably administered.

The moment of administration of the single administration dose before birth/calving may be determined by calculation if the day of insemination is known. The gestation period of cows is generally 279-292 days and may be more precisely known for a specific cow breed. Accordingly, the composition of the invention may be administered as a single administration dose 277 to 290 days after insemination, for example 280 days after insemination.

In the prophylactic methods and the methods of treatment of the invention, the composition of the invention is preferably administered to a subject in need thereof. The subject may be a human or one of the above-specified animals. If the method concerns in particular the prevention and/or treatment of milk fever, the subject is selected from cattle, in particular from a cow, sheep or goat, preferably from a gestating animal.

The amount of 1,25-(OH)$_2$ vitamin D$_3$ to be administered may be determined by the skilled person in dependence of the circumstances and/or the subject in question. As a guideline, 50 ng to 1.5 µg, preferably 100 ng to 1.3 µg, 200 ng to 1.0 µg, more preferably 300 to 800 ng, most preferably 400 to 700 ng, for example 350 to 600 ng 1,25-(OH)$_2$ vitamin D$_3$-glycosides may be administered per kg bodyweight of the subject. These amounts may apply for cows, for example.

The present invention will now be illustrated by way of examples. These examples do not limit the scope of this invention, which is defined by the appended claims.

EXAMPLES

Examples 1 and 2: Preparation of Extracts from *Solanum glaucophyllum*

Example 1: Extract Obtained by Maceration 300 kg dry leaves *S. glaucophyllum* were grinded to 10-15 mm particle size. The power was added to a solvent mixture and ethanol in a ratio of 7:3 (water:alcohol, v:v) and at a weight ratio of 1:10 (powdered dried leaves:solvent) and stirred for 10 hours at 40° C. for extraction.

The liquid phase is separated by filtration and the process is repeated up to twice using the same leaves.

At the end, 0.5 wt-% of ascorbic acid is added as an antioxidant and pH is adjusted to 6 using acetic acid. The entire liquid phase is evaporated in a thin-layer evaporator to a dry-matter content of approx. 35 wt. %.

The concentrated extract is analyzed and the concentration of 1,25-$(OH)_2$ vitamin $D_3$-glycosides is determined. The eluate is heat-treated (UHT) for removing germs. Maltodextrin (Ph. Eur. quality) is added to adjust the content of the active principle (total 1,25-(OH)2 vitamin D3) to a content of 50 gg/g (dry matter). The solution is spray-dried to dryness.

Example 2: Extract Obtained by Percolation

The same mixture of dried leaves and solvent mixture as used in Example 1 is percolated in a commercially available percolator for 8 hours at 35-45° C.

The liquid phase (raw extract) is further treated as described in Example I to yield the same final product as in Example 1.

Examples 3 and 4: Instant and Retard Release Formulations Containing the Extract Example 3: Instant Release Tablet Containing *S. glaucophyllum* Extract The ingredients listed in Table 4 below were mixed and pressed to an instant release tablet.

TABLE 4

| Composition of instant release tablet | |
|---|---|
| Ingredients | (mg/tablet) |
| Dried extract of Example 1 | 270 |
| Avicel 102 (mikrokristalline Cellulose) | 50 |
| Kollidon CL | 100 |
| Mg-Stearat veg. | 4 |
| Aerosil 200 | 7 |
| Total weight | 431 |

Example 4: Retard Release Tablet Containing *S. glaucophyllum* Extract

The ingredients listed in Table 5 below were mixed and pressed to a retard release tablet. The characteristics of the tablet are listed further below in Table 5.

TABLE 5

| Composition of retard release tablet | |
|---|---|
| Ingredients | (mg/tablet) |
| Dried extract of Example 1 | 270 |
| HPMC (100M) | 400 |
| Eudragit RS | 130 |
| Mg-Stearat veg. | 8 |
| S02, kolloidal | 8 |
| Total weight (target) | 830 |
| Average actual weight (mg) | 831.2 |
| hardness/tablet (N) | ca. 170 |
| dimension (mm) | 18 × 8.5 × 6.9 |

TABLE 5-continued

| Composition of retard release tablet | |
|---|---|
| Ingredients | (mg/tablet) |
| LOD (loss on drying tablet mixture) (%) | 2.89 |
| Charge size | 435 tablets |
| Yield (acceptable tablets) | 290 tablets |
| Yield (%) | 66.7 |

The polymer Eudragit has the property of soaking in contact with the rumen liquid and thereby releasing the soluble extract of Example 1 slowly.

Each tablet contains 50 ng analytically determined 1.25 $(OH)_2$ vitamin $D_3$ per 10 mg tablet.

In other words, a tablet of, for example, 430 mg contains 21.5 μg 1,25-$(OH)_2$ vitamin $D_3$.

Figure 1:
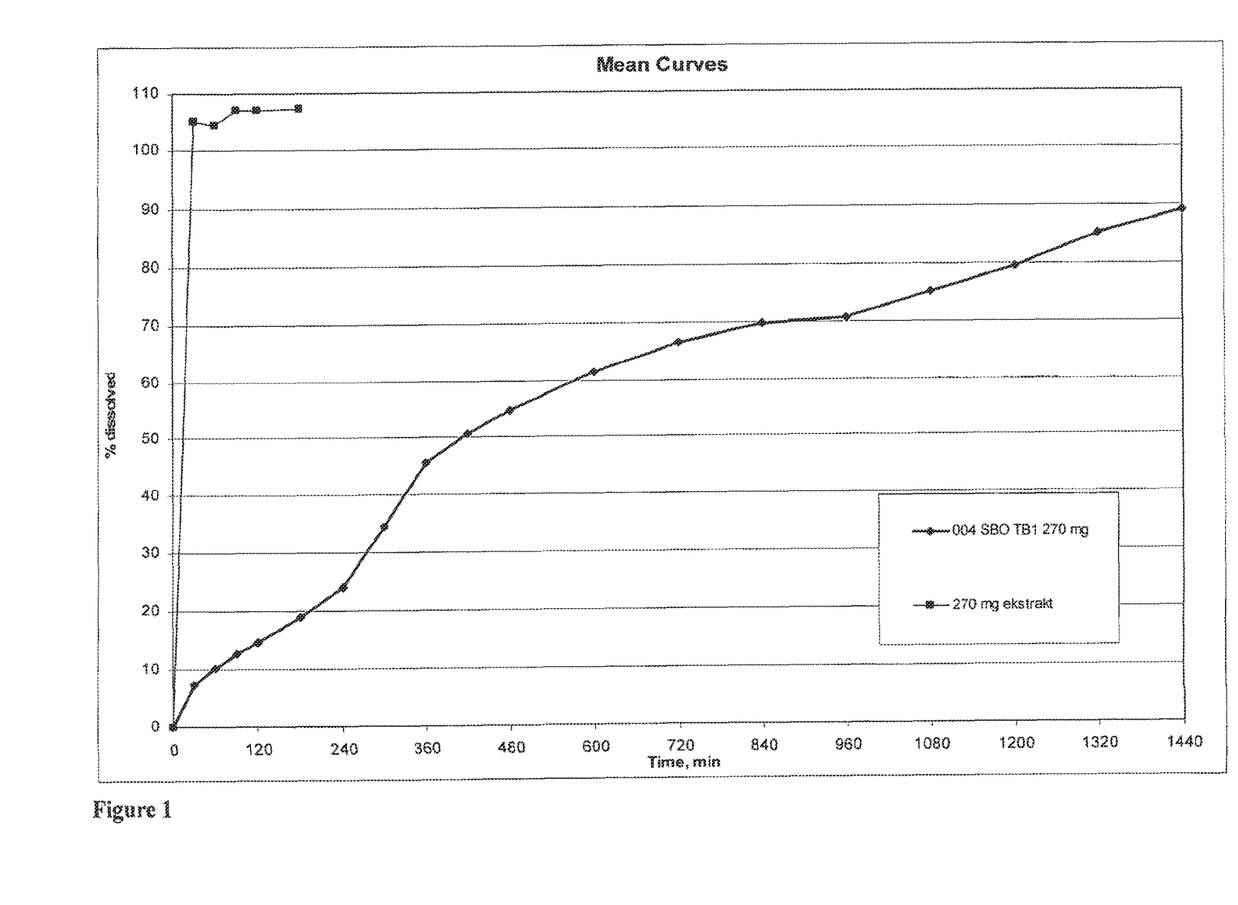
FIG. 1 compares in vitro release of an instant release formulation with a retard release formulation in accordance with the present invention (tablets) when added to a dissolution medium (US Pharmacopeia). The release is monitored by online measurement of absorption at 300 rim by a spectrophotometer and compared to absorption measured when adding a *S. glaucophyllum* dry extract directly to water.

The retard release characteristics were evaluated by a standard USP dissolution test (USP basket, 900 ml water, 300 nm) (for further details, see indications in this specification further above). Dissolution was measured by monitoring the time-dependent increase in absorption at 300 nm in a spectrophotometer. The increase in absorption is considered as the release of the extract into solution. The results are shown in FIG. 1. It can be seen that the retard release formulation is able to release 1,25-$(OH)_2$ vitamin $D_3$-glycosides contained in the *S. glaucophyllum* extract in a linear fashion for a period lasting over than 24 hours (1440 minutes), while the same active principle is liberated from the fast release form in less than 30 minutes.

Figure 2:
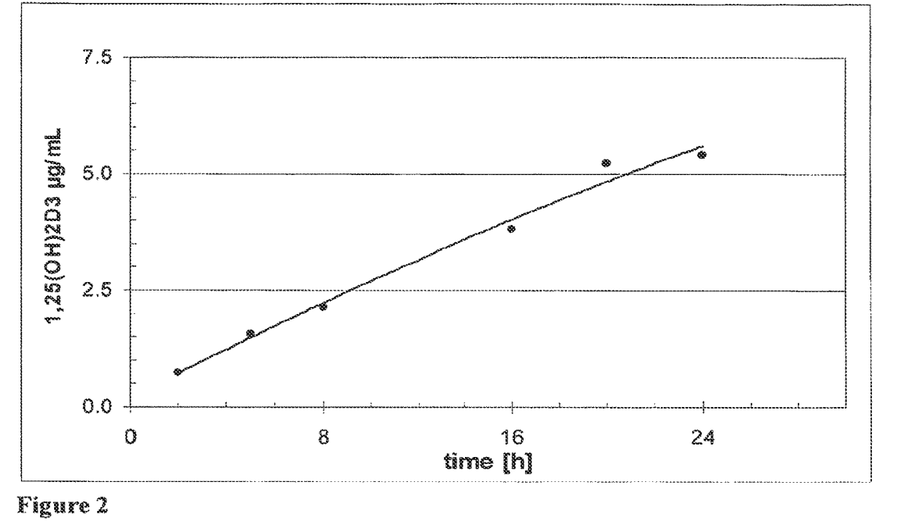
FIG. 2 shows in vitro release of a retard release formulation in accordance with the present invention (tablets) when added to the dissolution medium. The release is determined by measuring the concentration of the released $1,25\text{-(OH)}_2$ vitamin $D_3$-glycosides in the water repeatedly over time.

Furthermore, the concentration of the released active principle (1,25-(OH)2 vitamin $D_3$-glycosides) was measured at different times following addition of the tablet to the dissolution medium. The result is shown in FIG. 2 and the outcome is analogue to FIG. 1.

Figure 3:
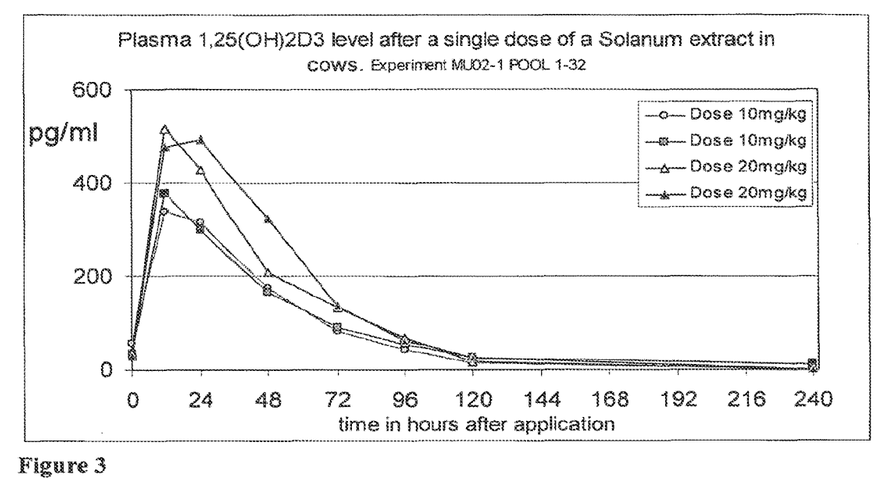
FIG. 3 shows the evolution of blood concentration of (1,25-(OH)$_2$ vitamin D$_3$-glycosides) in non-calving cows following a single administration of a *S. glaucophyllum* extract. Two different treatments were conducted, with half of the cows receiving 10 mg extract per kg animal weight and the other group 20 mg/kg. Three (3) to 4 cows having received the same dose were grouped and are shown in FIG. 3 (triangles: 20 mg/kg; circles and squares: 10 mg/kg). The rapid increase of blood 1,25-(OH)$_2$ vitamin D$_3$ levels following administration can be seen.

Example 5: Blood Levels of Active 1,25-(OH)2 Vitamin D Following Single Administration of Two Different Doses of the Plant Extract Twenty cows were allocated in two groups of 10 animals. Each cow received a single administration of a capsule containing 10 mg (group 1) or 20 mg (group 2) *S. glaucophyllum* extract of Example 1 per kg weight of the animal. Blood samples were collected before and at different times following administration and 1,25-$(OH)_2$ vitamin $D_3$ concentration was determined using an ELISA test kit (Immundiagnistik Bensheim, Germany). Groups of 3 and 4 animals of each treatment were pooled and the results are shown in FIG. 3. As can be seen, the plant extract significantly increases serum 1,25-$(OH)_2$ vitamin $D_3$ concentration in a dose-dependent manner. Again, no side effects of the treatment were observed.

Example 6: In Vivo Experiment Using the Composition of the Invention

Twenty-five cows of the races brown, Fleckvieh and Holstein of a weight of approximately 500-600 kg weight and including lactating and non-lactating subjects were allocated to 5 treatment groups as detailed in Table 6 blow. The animals were given a single dose of the test preparation orally per bolus. Blood was taken at time 0 (before application) and at days 1, 2, 3, 4, 5, 7, 9 and 11 following application. From the blood, serum was prepared and calcium (total), phosphate and 1,25-$(OH)_2$ vitamin $D_3$ was analyzed according to established clinico-chemical methods.

Treatment: all test preparations were applied to the animal as one single bolus in a gelatine capsule (length 7 cm, diameter 2.2 cm and volume 24 mL, Capsula GmbH, Ratingen, Germany) with the aid of a usual bolus applicator. The volume that was not filled with tablets was filled up with pectin as inert excipient. The control group only received pectin.

The boluses contained, in accordance with the treatment group, instant release tablets as described in Example 3 (groups 2 and 4) and retard release tablets as prepared in Example 4 (groups 1 and 4).

TABLE 6

Treatment groups

| Group | Preparation | Dose |
|---|---|---|
| 1 | Retard release form of the *Solanum glaucophyllum* extract | 10 mg/kg body weight, (corresponds to 500 ng 1,25-(OH)$_2$ vitamin D3) |
| 2 | Instant release form of the *Solanum glaucophyllum* extract. | 10 mg/kg body weight (corresponds to 500 ng 1,25-(OH)$_2$ vitamin D$_3$) |
| 3 | Synthetic 1,25-(OH)$_2$ vitamin D$_3$ (Cerbios Pharma SA Barbengo, Switzerland) | 500 ng 1,25-(OH)$_2$ vitamin D$_3$) |
| 4 | Combination of retard- and instant release Forms | 5 + 5 mg/kg body weight (corresponds to 500 ng 1,25-(OH)$_2$ vitamin D$_3$) |
| 5 | Control | Pectin as inert excipient |

The results of these experiments are presented in Tables 7-9 below showing the serum calcium, phosphate and 1,25-(OH)$_2$ vitamin D$_3$ concentrations determined in each group and the outcome of the statistical comparison of the treatments.

TABLE 7

Serum calcium in mmol/L (mean t standard deviation) at days 0, 1, 2, 3, 4, 5, 7, 9, 11 in treatment grouns (n = 5).
Serum calcium (nmol/l)

| day | Group 1 | Group 2 | Group 3 | Group 4 | Group 5 |
|---|---|---|---|---|---|
| 0 | 2.47 ± 0.06 | 2.50 ± 0.06 | 2.40 ± 0.2 | 2.46 ± 0.11 | 2.40 ± 0.06 |
| 1 | 2.75 ± 0.06 cE | 2.67 ± 0.03 E | 2.64 ± 0.05 E | 2.68 ± 0.12 e | 2.44 ± 0.09 |
| 2 | 2.89 ± 0.07 bCE | 2.74 ± 0.07 E | 2.67 ± 0.09 Ed | 2.81 ± 0.12 E | 2.39 ± 0.02 |
| 3 | 2.82 ± 0.06 cE | 2.75 ± 0.11 E | 2.72 ± 0.09 E | 2.81 ± 0.08 E | 2.42 ± 0.03 |
| 4 | 2.86 ± 0.03 BCE | 2.72 ± 0.06 E | 2.72 ± 0.06 E | 2.78 ± 0.10 E | 2.45 ± 0.05 |
| 5 | 2.81 ± 0.06 CE | 2.64 ± 0.16 e | 2.61 ± 0.02 E | 2.76 ± 0.11 E | 2.46 ± 0.03 |
| 7 | 2.77 ± 0.09 bCE | 2.60 ± 0.11 | 2.57 ± 0.06 e | 2.71 ± 0.16 e | 2.44 ± 0.06 |
| 9 | 2.64 ± 0.12 E | 2.59 ± 0.07 E | 2.56 ± 0.09 | 2.57 ± 0.11 | 2.46 ± 0.02 |
| 11 | 2.48 ± 0.12 | 2.44 ± 0.06 | 2.45 ± 0.02 | 2.45 ± 0.05 | 2.40 ± 0.05 |

$^a$(p < 0.05)   $^A$(p < 0.01)   vs G1 (SR form alone)
b (p < 0.05)   B(p < 0.01)   vs G2 (IR form alone)
c (p < 0.05)   C(p < 0.01)   vs G3 (1,25(OH)$_2$D$_3$)
d (p < 0.05)   $^D$(p < 0.01)   vs G4 (combination)
e (p < 0.05)   E (p < 0.01)   vs G5 (control)

TABLE 8

Serum phosphate in mmol/L (mean t standard deviation) at days 0, 1, 2, 3, 4, 5, 7, 9, 11 in treatment groups (n = 5).
Serum phophorus (m/mol/1)

| day | Group 1 | Group 2 | Group 3 | Group 4 | Group 5 |
|---|---|---|---|---|---|
| 0 | 2.33 ± 0.11 | 2.44 ± 0.06 ce | 2.30 ± 0.07 | 2.35 ± 0.38 | 2.24 ± 0.17 |
| 1 | 2.98 ± 0.18 CE | 2.84 ± 0.18 CE | 2.50 ± 0.12 ed | 2.85 ± 0.24 E | 2.07 ± 0.30 |
| 2 | 3.30 ± 0.10 CE | 3.25 ± 0.21 E | 2.81 ± 0.25 ED | 3.41 ± 0.15 E | 2.12 ± 0.21 |
| 3 | 3.51 ± 0.17 cE | 3.41 ± 0.23 cE | 3.05 ± 0.19 Ed | 3.38 ± 0.21 E | 2.22 ± 0.18 |
| 4 | 3.47 ± 0.29 E | 3.45 ± 0.53 E | 3.24 ± 0.34 E | 3.43 ± 0.12 E | 2.38 ± 0.22 |
| 5 | 2.94 ± 0.10 Ed | 2.71 ± 0.41 ed | 2.60 ± 0.32 E | 3.17 ± 0.12 E | 2.05 ± 0.15 |
| 7 | 2.98 ± 0.17 CE | 2.66 ± 0.35 E | 2.43 ± 0.23 e | 2.89 ± 0.19 E | 2.06 ± 0.10 |
| 9 | 2.63 ± 0.25 bcE | 2.10 ± 0.16 d | 2.05 ± 0.44 | 2.43 ± 0.24 e | 1.97 ± 0.08 |
| 11 | 2.47 ± 0.23 E | 2.26 ± 0.34 | 2.10 ± 0.16 | 2.43 ± 0.27 | 2.10 ± 0.06 |

$^a$(p < 0.05)   $^A$(p < 0.01)   vs G1 (SR form alone)
b (p < 0.05)   $^B$(p < 0.01)   vs G2 (IR form alone)
c (p < 0.05)   C (p < 0.01)   vs G3 (1,25(OH)2D3)
d (p < 0.05)   D (p < 0.01)   vs G4 (combination)
e (p < 0.05)   E (p < 0.01)   vs G5 (control)

TABLE 9

Serum 1,25-(OH)$_2$ vitamin D$_3$ in pg/mL (mean of pooled serum samples) at days 0, 1, 2, 3, 4, 5, 7, 9, 11 in treatment groups n = 5.

Serum 1,25-dihydroxyvitamin D$_3$

| day | Group 1 | Group 2 | Group 3 | Group 4 | Group 5 |
|---|---|---|---|---|---|
| 0 | 58 | 30 | 20 | 47 | 30 |
| 1 | 364 | 291 | 243 | 243 | 10 |
| 2 | 216 | 156 | 150 | 148 | 30 |
| 3 | 96 | 58 | 56 | 110 | 36 |
| 4 | 67 | 28 | 40 | 37 | 8 |
| 5 | 35 | 53 | 46 | 16 | 28 |
| 7 | 36 | 34 | 30 | 20 | 19 |
| 9 | 41 | 22 | 23 | 4 | 20 |
| 11 | 40 | 16 | 25 | 1 | 21 |

Figure 4:
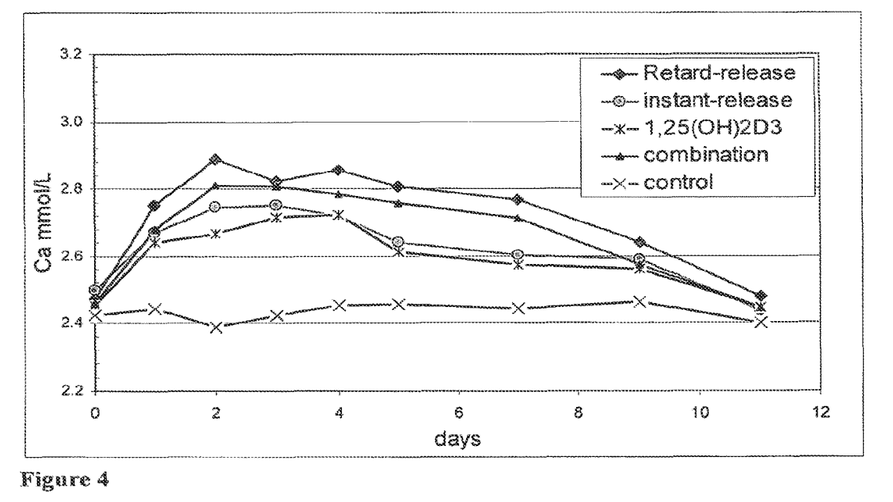
FIG. 4 shows serum calcium levels of cows following oral administration of different treatments, namely: a retard release formulation according to an embodiment of the invention containing a *S. glaucophyllum* extract with a determined amount of 1,25-(OH)$_2$ vitamin D$_3$-glycosides (rhombi, "Retard-release"), the dry extract directly (filled circles, "instant-release"); an equivalent amount of synthetic 1,25-(OH)$_2$ vitamine D$_3$ ("1,25(OH)2D3", *); and a composition containing a retard and an instant release formulation of the *S. glaucophyllum* extract (filled triangles, "combination"). Treatments containing the retard release formulation in accordance with the invention resulted in the highest serum calcium concentration over the entire period. The bottom line is the control (*).
Figure 5:
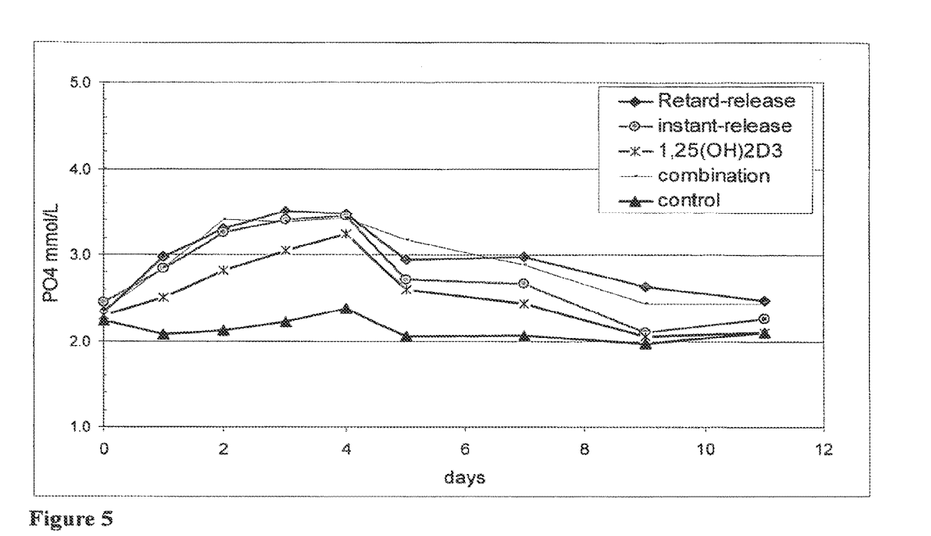
FIG. 5 shows serum phosphate levels determined in the same experiment as described for FIG. 4. The legend is shown in the Figure.
Figure 6:
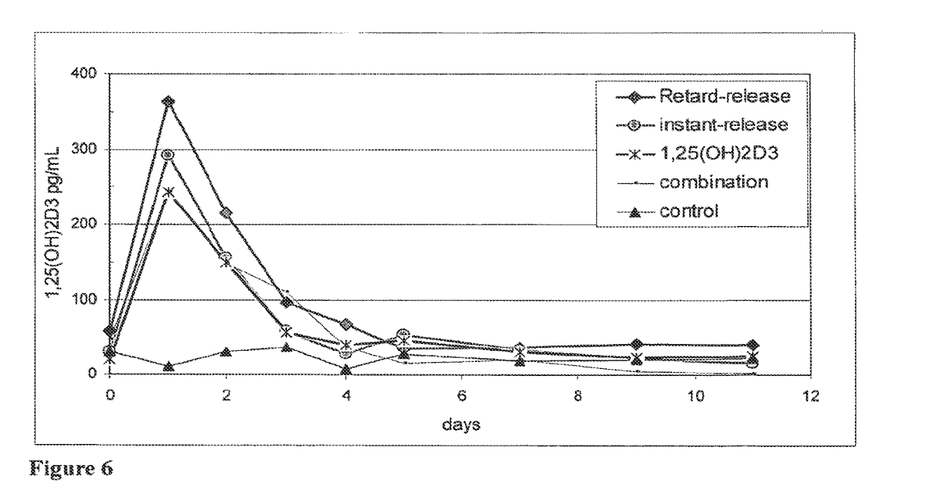
FIG. 6 shows serum 1,25-(OH)$_2$ vitamin D$_3$ levels determined in the same experiment as described for FIG. 4. The legend is shown in the Figure.

All treatments showed an increase in serum calcium and phosphate within 24 hours and lasted until 9 days. All groups that received the *S. glaucophyllum* extracts showed a higher concentrations of 1,25-(OH)$_2$ vitamin D$_3$, calcium and phosphorous in serum than the group with synthetic 1,25-(OH)$_2$ vitamin D$_3$. In addition, the effect of the retard release form and the combination was stronger than the effect of the instant release form of the extract. The outcome is also presented in FIG. 4 (serum calcium), FIG. 5 (serum phosphate) as the effect of the treatment and in FIG. 6 (serum 1,25-(OH)$_2$ vitamin D$_3$) as the cause of the effect.

Example 7: In Vivo Experiment in Gestating Cows, Application Before Birth

In this experiment, a single dose of the inventive composition (Slbv) was compared with the state-of-the-art treatment for milk fever prevention (Bc). All animals in this experiment were randomly selected from 5 different farms. All animals were German Fleckvieh, aged between 2 and 8 years and had between 1 and 7 calvings and were randomly attributed to treatment A (Bc) and treatment B (Slbv). Apart from the usual reduction of the calcium content in the diet before birth, no prophylaxis for milk fever was done.

The animals were all gestating cows and the treatments were administered when calving was expected to occur within 72 hours (sampling 1). The days until effective calving were determined and finally varied from 1 to 12 days between the cows.

Treatment: Group A (Bc)

Application of 4 boli of a calcium salt represented as Bovikalc® (Boehringer Ingelheim, Germany, 43 g calcium per bolus). According to producers recommendations: a first Bolus 24 hours a.p., a second bolus around partum, a third bolus 12 to 15 hours after calving and a fourth bolus 24 to 30 hours after calving.

Treatment: Group B (Slbv)

Figure 10:
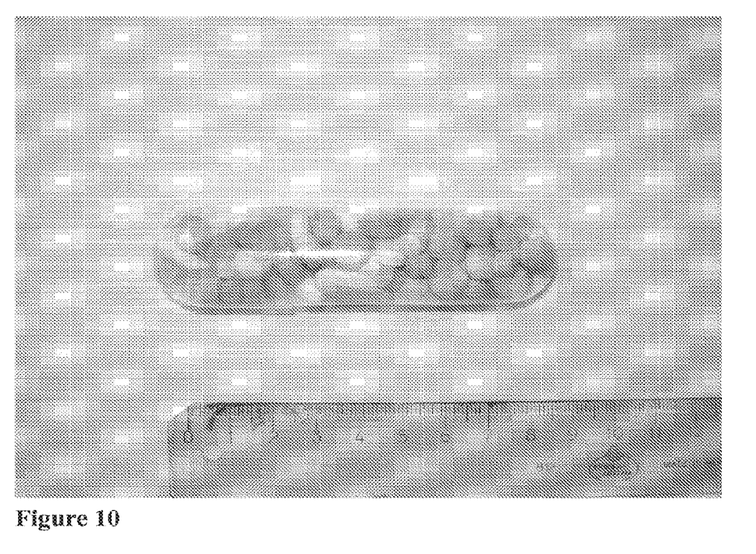
FIG. 10 shows an embodiment of the composition of the present invention, provided in the form of an experimental bolus adapted to cows. The bolus is suitable to prevent milk fever in gestating cows if administered within 4 to 2 days before birth. The bolus is made from a transparent gelatine capsule and contains retard release tablets (large dark tablets), instant release tablets (small dark tablets) and dolomite capsules (large, longish white tablets). Before administration, the bolus may be filled with filler.

Application of a single dose of a preparation containing:
7 g extract of *S. glaucophyllum* from instant release tablets (Example 3; Table 4);
14 g extract of *S. glaucophyllum* retard release tablets (Example 4; Table 5);
16 g activated dolomite;
altogether packed in 2 gelatin capsules (cf. FIG. 10). The application was given within 72 to 24 hours ante partum (a.p.). Animals were calving occurred longer than 96 hours after application were excluded from the evaluation in this experiment.

In all animals, serum calcium, phosphate and 1,25-(OH)$_2$ vitamin D$_3$ was determined from samples taken before birth and at intervals of 2 days after birth for 7 days (samplings 2-5). Analysis was done using typical clinico-chemical methods.

Results: Group A

All 25 animals in this treatment fulfilled the criteria of correct dosing (the administration time ante partum). One animal showed signs of milk fever.

Results: Group B

Of the 31 animals in this treatment, 26 animals fulfilled the criteria of receiving treatment within 72 to 24 hours a.p. None of these animals showed signs of milk fever. One animal showed signs of milk fever and one animal died because of other reasons not related to the present study.

Figure 7:
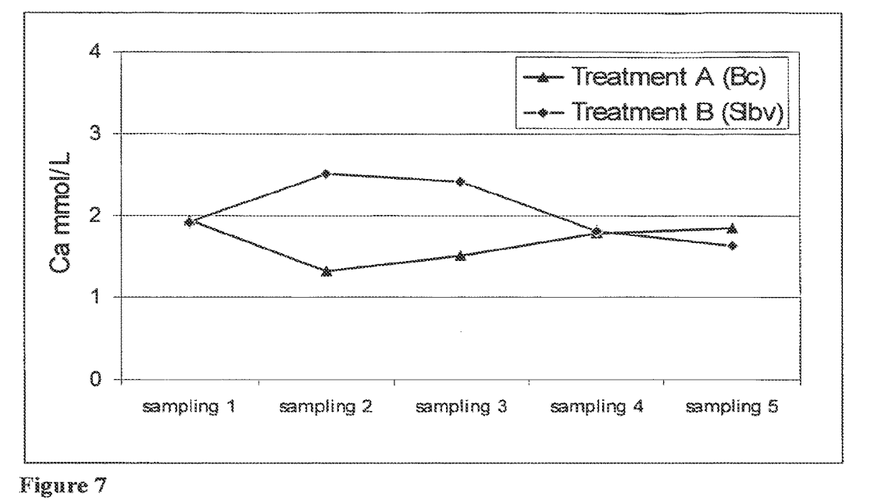
FIG. 7 shows serum calcium levels over time before (sampling 1) the first administration in cows receiving repeatedly a commercially available calcium formulation (triangles; Bc) in comparison to cows receiving a single administration dose of the composition of the present invention (filled rhombi). Samples were taken at intervals of two days following calving (samplings 2-5). As can be seen, a single administration of the composition of the invention had a more profound effect on blood calcium and phosphate as the repeated administration of the commercially available calcium formulation.
Figure 8:
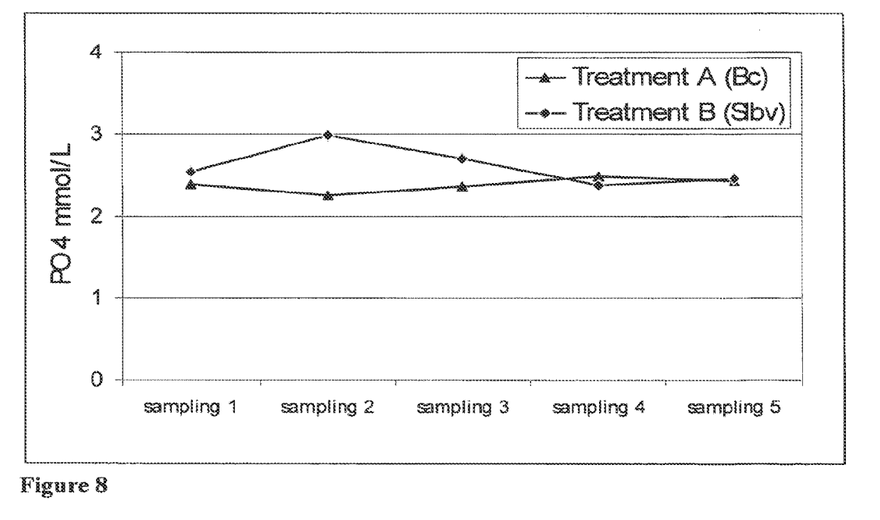
FIG. 8 is as FIG. 7, but showing serum phosphate levels. The data obtained on the basis of the composition of the invention are shown as rhombi.
Figure 9:
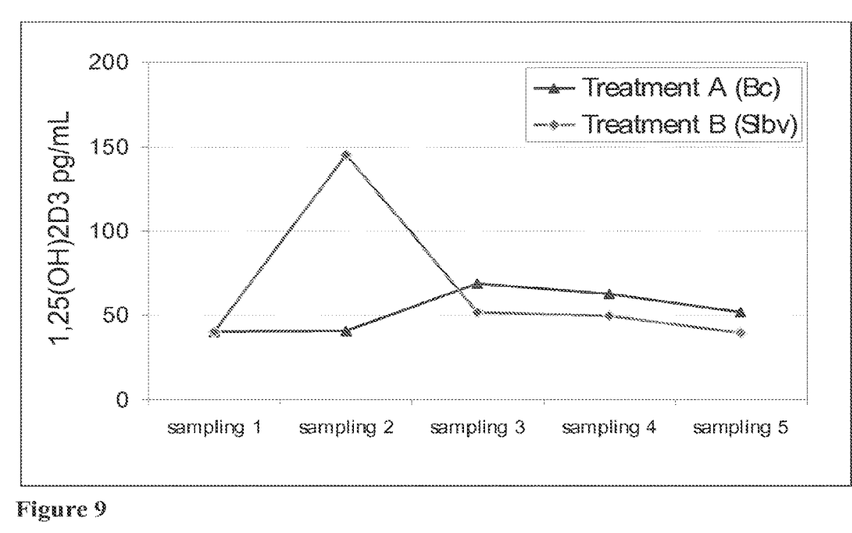
FIG. 9 is as FIGS. 7 and 8, but showing serum 1,25-(OH)$_2$ vitamin D$_3$ levels. The data obtained on the basis of composition of the invention are shown as rhombi.

The results of the serum calcium, phosphate and 1,25-(OH)$_2$ vitamin D$_3$ is seen in FIGS. 7-9, respectively.

In conclusion, a single administration of the composition of the invention yields as good or better results as the administration of four doses of a commercially available calcium preparation intended for the prevention of milk fever in cows.

The invention is claimed as follows:

1. A method for preventing parturient paresis in a gestating ruminant at risk thereof, the method comprising:
administering orally to the gestating ruminant 72 to 24 hours before birth a single dose of a pharmaceutical or veterinary composition comprising a slow release formulation and an instant release formulation, each formulation comprising a source of 1,25-(OH)$_2$ vitamin D$_3$-glycosides that is a *Solanum glaucophyllum* extract obtained by maceration or percolation of dried leaves of the *Solanum glaucophyllum* with a solvent, the *Solanum glaucophyllum* extract being totally free of solanine, chaconine and solasodine, the pharmaceutical or veterinary composition is administered to the gestating ruminant only once and in an amount providing 50 ng to 1.5 µg of the 1,25-(OH)$_2$ vitamin D$_3$-glycosides per kg bodyweight of the gestating ruminant, the composition comprises the slow release formulation and the instant release formulation in a ratio from 1:1 to 4:1 as a weight ratio of the 1,25-(OH)$_2$ vitamin D$_3$-glycosides present in the slow release formulation relative to the 1,25-(OH)$_2$ vitamin D$_3$-glycosides present in the instant release formulation,
the composition further comprising dolomite as the only calcium source in the composition, and the composition has a density of at least 1.2 g/ml,
the dolomite is 70-85 wt. % of the slow release formulation, the slow release formulation comprises a binder that is up to 5 wt. % of the slow release formulation and comprises hydroxypropylmethylcellulose (HPMC) and optionally polyvinylpyrrolidone (PVP), the *Solanum glaucophyllum* extract in the slow release formulation is (i) included in a matrix containing poly(meth)acrylate-methyl/ethyl/2-trimethyl amino ethyl estercopolymerisate or (ii) has a coating comprising poly(meth)acrylate-methyl/ethyl/2-trimethyl amino ethyl estercopolymerisate, and the slow release formulation comprises an amount of the poly(meth)acrylate-methyl/ethyl/2-trimethyl amino ethyl estercopolymerisate that completely releases 1,25-(OH)$_2$ vitamin D$_3$-glycosides contained in the slow release formulation over a time period that is at least 4 hours as determined in vitro by immersion of the slow release formulation into water at 37° C. and determining the time until all the 1,25-(OH)$_2$ vitamin D$_3$-glycosides contained in the slow release formulation are dissolved in the water, the dolomite is 0-87.5 wt. % of the instant release formulation, and the instant release formulation comprises an excipient which following contact with water and/or a digestive liquid completely releases the 1,25-(OH)$_2$ vitamin D$_3$-glycosides contained in the instant release formulation over a time period that is less than 4 hours as determined in vitro by immersion of the instant release formulation into water at 37° C. and determining the time until all the 1,25-(OH)$_2$ vitamin D$_3$-glycosides contained in the instant release formulation are dissolved in the water, the excipient in the instant release formulation comprises a binder that is up to 10 wt. % of the instant release formulation and comprises HPMC and optionally PVP.

2. The method of claim 1, wherein the 1,25-(OH)$_2$ vitamin D$_3$-glycosides from the *S. glaucophyllum* are the only active form of vitamin D3 present in the composition.

3. The method of claim 1, wherein the slow release formulation and the instant release formulation each have a density of at least 1.2 kg/l.

4. The method of claim 1, wherein the composition is in a form selected from the group consisting of a bolus, a capsule, a granular composition, a pellet, a tablet, a gel, a powder, and a compacted powder.

5. The method of claim 1, wherein the coating releases the 1,25-(OH)$_2$ vitamin D$_3$-glycosides from the slow release formulation by a process selected from the group consisting of (i) diffusion of the 1,25-(OH)$_2$ vitamin D$_3$-glycosides through the coating, (ii) enzymatic decomposition of the coating in specific compartments of the digestive tract, and (iii) a combination thereof.

6. The method of claim 1, wherein the slow release formulation comprises an amount of the poly(meth)acrylate-methyl/ethyl/2-trimethyl amino ethyl estercopolymerisate such that the matrix is eroded completely over the time period that is at least 4 hours.

7. The method of claim 1, wherein the slow release formulation comprises an amount of the poly(meth)acrylate-methyl/ethyl/2-trimethyl amino ethyl estercopolymerisate such that the coating is resistant to the digestive liquid of the stomach but is decomposed when in contact with bile and/or pancreatic juice.

8. The method of claim 1, wherein the excipient in the instant release formulation further comprises at least one disintegrant selected from the group consisting of a sodium salt of carboxymethylcellulose, a sodium salt of carboxymethylated starch, crosslinked PVP, starch and mixtures thereof.

9. The method of claim 8, wherein the sodium salt of carboxymethylcellulose is 1-5 wt. % of the instant release formulation, the sodium salt of carboxymethylated starch is 2-8 wt. % of the instant release formulation, the crosslinked PVP is 0.5-5 wt. % of the instant release formulation, and the starch is 2-10 wt. % of the instant release formulation.

10. The method of claim 1, wherein the excipient in the instant release formulation comprises a filler that is up to 42.5 wt. % of the instant release formulation and selected from the group consisting of lactose, microcrystalline cellulose and a mixture thereof.

11. The method of claim 1, wherein the slow release formulation comprises a filler that is up to 15 wt. % of the slow release formulation and selected from the group consisting of lactose, microcrystalline cellulose and a mixture thereof.

12. The method of claim 1, wherein the *Solanum glaucophyllum* extract is 10-20 wt. % of the slow release formulation.

13. The method of claim 1, wherein the *Solanum glaucophyllum* extract is 12.5 wt. % of the instant release formulation.

14. The method of claim 1, wherein the single dose of the composition is administered in an amount providing 350 ng to 600 ng of the 1,25-(OH)$_2$ vitamin D$_3$-glycosides per kg bodyweight of the gestating ruminant.

15. A method for preventing parturient paresis in a gestating ruminant at risk thereof, the method comprising:
administering orally to the gestating ruminant 72 to 24 hours before birth a single dose of a pharmaceutical or veterinary composition comprising a slow release formulation and an instant release formulation, each formulation comprising a source of 1,25-(OH)$_2$ vitamin D$_3$-glycosides that is a *Solanum glaucophyllum* extract obtained by maceration or percolation of dried leaves of the *Solanum glaucophyllum* with a solvent, the *Solanum glaucophyllum* extract being totally free of solanine, chaconine and solasodine, the pharmaceutical or veterinary composition is administered to the gestating ruminant only once and in an amount providing 50 ng to 1.5 µg of the 1,25-(OH)$_2$ vitamin D$_3$-glycosides per kg bodyweight of the gestating ruminant, the composition comprises the slow release formulation and the instant release formulation in a ratio from 1:1 to 4:1 as a weight ratio of the 1,25-(OH)$_2$ vitamin D$_3$-glycosides present in the slow release formulation relative to the 1,25-(OH)$_2$ vitamin D$_3$-glycosides present in the instant release formulation,
the composition further comprising dolomite as the only calcium source in the composition, and the composition has a density of at least 1.2 g/ml,
the dolomite is 8.3-25.0 wt. % of the slow release formulation, the slow release formulation comprises a binder that is up to 8.3 wt. % of the slow release formulation and comprises HPMC and optionally PVP, the *Solanum glaucophyllum* extract in the slow release formulation is (i) included in a matrix containing polymethacrylate-methyl/butyl/2-dimethyl aminoethyl ester-copolymerisate or (ii) has a coating comprising polymethacrylate-methyl/butyl/2-dimethyl aminoethyl ester-copolymerisate, and the slow release formulation comprises an amount of the polymethacrylate-methyl/butyl/2-dimethyl aminoethyl ester-copolymerisate that completely releases 1,25-(OH)$_2$ vitamin D$_3$-glycosides contained in the slow release formulation over a time period that is at least 4 hours as determined in vitro by immersion of the slow release formulation into water at 37° C. and determining the time until all the 1,25-(OH)$_2$ vitamin D$_3$-glycosides contained in the slow release formulation are dissolved in the water,
the dolomite is 0-87.5 wt. % of the instant release formulation, and the instant release formulation comprises an excipient which following contact with water and/or a digestive liquid completely releases the 1,25-(OH)$_2$ vitamin D$_3$-glycosides contained in the instant release formulation over a time period that is less than 4 hours as determined in vitro by immersion of the instant release formulation into water at 37° C. and determining the time until all the 1,25-(OH)$_2$ vitamin D$_3$-glycosides contained in the instant release formulation are dissolved in the water, the excipient in the instant release formulation comprises a binder that is up to 10 wt. % of the instant release formulation and comprises HPMC and optionally PVP.

16. The method of claim 15, wherein the slow release formulation comprises a filler that is 50-75 wt. % of the slow release formulation and selected from the group consisting of lactose, microcrystalline cellulose and a mixture thereof.

17. The method of claim 15, wherein the *Solanum glaucophyllum* extract is 16.7 wt. % of the slow release formulation.

18. The method of claim 15, wherein the *Solanum glaucophyllum* extract is 12.5 wt. % of the instant release formulation.

19. The method of claim 15, wherein the single dose of the composition is administered in an amount providing 350 ng to 600 ng of the 1,25-$(OH)_2$ vitamin $D_3$-glycosides per kg bodyweight of the gestating ruminant.

* * * * *